(12) United States Patent
Thorel (10) Patent No.: US 11,813,350 B2
(45) Date of Patent: Nov. 14, 2023

(54) COMPOSITION FOR THE TREATMENT OF ROSACEA AND/OR TELANGIECTASIA

(71) Applicants: NAOS INSTITUTE OF LIFE SCIENCE, Aix-en-Provence (FR); Jean-Noël Thorel, Paris (FR)

(72) Inventor: Jean-Noël Thorel, Paris (FR)

(73) Assignees: Jean-Noël Thorel, Paris (FR); NAOS INSTITUTE OF LIFE SCIENCE, Aix-En-Provence (FR)

( * ) Notice: Subject to any disclaimer, the term of this patent is extended or adjusted under 35 U.S.C. 154(b) by 58 days.

(21) Appl. No.: 17/521,064

(22) Filed: Nov. 8, 2021

(65) Prior Publication Data

US 2022/0142901 A1    May 12, 2022

(30) Foreign Application Priority Data

Nov. 10, 2020  (FR) ...................................... 2011519

(51) Int. Cl.
*A61K 8/73*   (2006.01)
*A61Q 19/02*  (2006.01)

(52) U.S. Cl.
CPC ................ *A61K 8/732* (2013.01); *A61K 8/73* (2013.01); *A61Q 19/02* (2013.01)

(58) Field of Classification Search
CPC .......... A61K 8/732; A61K 8/73; A61Q 19/02
See application file for complete search history.

(56) References Cited

U.S. PATENT DOCUMENTS 5,912,330 A       6/1999  Tabuchi et al.
2020/0261531 A1* 8/2020  Carle ..................... A61P 17/10

FOREIGN PATENT DOCUMENTS

| CA | 2625725  C | * 3/2013 | ............... A61K 8/06 |
|----|-----------|----------|--------------------------|
| CN | 103735458 |   4/2014 |                          |
| EP | 1484051   |  12/2004 |                          |
| FR | 3022139   |  12/2015 |                          |

OTHER PUBLICATIONS

Search Report and Written Opinion (non-English) dated Jun. 30, 2021, from French Application No. 2011519, 12 pages.
Anonymous, "Maltooligosyl Glucoside", May 17, 2017, 2 pages.
Li, Y. et al. "Inhibitory effect of timolol on topical glucocorticoid-induced skin telangiectasia", Molecular Medicine Reports, 18:2823-2831, 2018.

* cited by examiner

*Primary Examiner* — Leigh C Maier
*Assistant Examiner* — Everett White
(74) *Attorney, Agent, or Firm* — Meunier Carlin & Curfman LLC (57) ABSTRACT

The invention relates to a composition comprising, as dermatological active principle, at least one polysaccharide consisting of a glucose and trehalose heteropolymer and a branched hydrogenated glucose homopolymer comprising $\alpha$ (1-4) and $\alpha$ (1-6) bonds, for use in the treatment of rosacea and/or telangiectasia.

13 Claims, 2 Drawing Sheets

COMPOSITION FOR THE TREATMENT OF ROSACEA AND/OR TELANGIECTASIA

TECHNICAL FIELD OF THE INVENTION

The invention relates to the field of dermatological care and, more particularly, the treatment of inflammatory skin conditions. More specifically, the invention relates to a composition, preferably cosmetic, for the treatment of rosacea and/or telangiectasia.

TECHNOLOGICAL BACKGROUND

The skin is the main barrier that separates the body from the external environment and is made up of the superposition of three main layers, respectively from the deepest to the most superficial: the hypodermis, the dermis and the epidermis. Several factors affect the health of the skin. Thus, and due to its constant interaction with the environment, the skin is subjected to multiple attacks (viruses, bacteria, UV rays, chemical attacks, extreme temperatures, etc.) which alter its balance. In parallel with these exogenous attacks, each individual has internal factors having an impact on the health of the skin, namely, genetic heritage or even hormones.

These various exogenous and endogenous factors can cause dermatological pathologies, in particular inflammatory skin conditions.

These inflammatory skin conditions, such as rosacea, cause feelings of physical discomfort. In addition, they can become a hindrance to social life. In other words, these conditions, especially rosacea and/or telangiectasia, are the cause of cosmetic and aesthetic drawbacks.

Regarding rosacea, all forms are visible and episodes of inflammatory flare-up as well as those of remission are unpredictable, which makes the disease difficult to control. Therefore, rosacea has a real impact on morale, social relationships and self-confidence.

Rosacea and rosacea-related skin pathologies are included in the list of chronic inflammatory skin diseases. Rosacea is characterized by redness on the cheeks, nose, forehead and chin. Rosacea and rosacea-related skin diseases affect the small vessels of the face. Therefore, they are not only characterized by redness, but also by visible vessels, and, in some more severe cases, by pimples and thickening of the skin.

Rosacea and rosacea-related diseases usually sensitize the skin and, in some cases, make it intolerant.

In addition to rosacea, there are therefore different forms of skin diseases linked to rosacea, including telangiectasia, flushes, couperose, ocular rosacea, papulopustular rosacea, the hypertrophic form, phymatous rosacea or even erythematotelangiectatic rosacea. However, rosacea and the diseases associated with this skin pathology should be distinguished from other skin conditions, such as psoriasis (red patches that flake off) or seborrheic dermatitis (which affects the sebaceous glands).

Telangiectasia is a pathology characterized by venules that become visible under the skin as they are dilated. These small vessels appear red or purplish. They can also be symptoms associated with vascular rosacea or couperose.

Rosacea manifests as erythema (occasional or persistent redness), couperose (also called telangiectasia) and/or papulopustules (skin lesions similar to acne lesions, but without comedones). At later stages, rosacea may be accompanied by hypertrophy of the nose (rhinophyma) or by ocular involvement.

The prevalence of rosacea remains highly variable between countries, populations studied and age. In Europe, the affected population is estimated to be between 2 and 10%. For example, in Germany the prevalence is estimated at 12.3%, in England at 1.8%, in the United States at 1.34%, and in France, between 2 and 3%.

Epidemiological studies show that people with fair skin and clear eyes are mostly affected. However, populations with a V and VI phototype may also be affected.

The exact causes of rosacea are still being defined but it has been firmly established that this condition is multifactorial in origin. While the contribution of the vascular component is obvious, it seems to have taken a back seat in recent years, behind the role of innate immunity which has been highlighted by numerous fundamental and clinico-biological studies. According to this scenario, now favored by most researchers in the field, abnormal stimulation of innate immunity results in the increase of inflammatory mediators and also in disruption of the barrier function of the skin.

Among the mediators of innate immunity that have been convincingly implicated in the etiology of rosacea, a key role was attributed to the antimicrobial peptide cathelicidin. Human cathelicidin is an antimicrobial peptide that plays an important role in the skin's defense against pathogens. This mediator is secreted as an 18 kDa propeptide, called hCAP18, which is biologically inactive. Proteolytic cleavage on the C-terminal side by proteases allows the release of the active antimicrobial form called LL-37, but also other peptide fragments.

There is a credible correlation between high levels of LL-37 in the epidermis and the onset of rosacea. In normal skin, the content of LL-37 peptide is low, while in the skin of patients with rosacea, the LL-37 peptide is present at a level 10 times higher than in controls in the epidermis. The LL-37 peptide targets Gram-positive and Gram-negative bacteria and also has antifungal activity. In addition to its antimicrobial activity, LL-37 exhibits pro-inflammatory properties through a chemoattractant effect on monocytes, neutrophils and T cells and affects angiogenesis. This pro-inflammatory effect helps the body respond better to attacks from pathogens, but at the same time, can exacerbate skin irritation.

The cleavage of the hCAP18 protein in its active pro-inflammatory form LL-37 is carried out by the kallikrein protease 5 (KLK-5). KLK-5 is a serine protease expressed by keratinocytes in normal skin. It has been shown that the lesion skin of subjects suffering from rosacea has a higher expression of the KLK-5 gene than that of the skin of healthy control subjects. It is interesting to note that this overexpression is correlated with that of cathelicidin.

Due to its ability to degrade the proteins that form the extracellular component of cell junctions in the stratum corneum, the KLK-5 enzyme also plays a role in the removal of corneocytes through desquamation. By virtue of its role in desquamation, an increased proteolytic activity of KLK-5 then leads to a progressive deterioration of the barrier function.

The enzymatic activity of KLK-5 is also regulated by matrix metalloproteinases (MMPs). Specifically, activation of KLK-5 occurs after cleavage of its proenzyme form by MMP-9. Notably, increased expression of MMP-2 and MMP-9 was observed in the skin of patients with rosacea. Such increased expression of MMPs has potential implications for the UV degeneration seen in rosacea. In addition, the initiation of activation of KLK-5 by MMPs leads to further activation of LL-37, the cleaved form of cathelicidin, thereby amplifying the pro-inflammatory cascade.

It has also been shown that the KLK-5 enzyme is able to activate PAR-2 (receptor activated by protease 2). This cellular receptor is strongly expressed by the keratinocytes of the granular layer, where it is involved in the regulation homeostasis of the skin barrier.

Skin samples from patients with rosacea demonstrated, after immunohistochemical staining, higher levels of PAR-2 expression than those from healthy subjects.

Activation of PAR-2 has several effects on the barrier function. In particular, it decreases intercellular adhesion by E-cadherin, which results in increased permeability of the epidermal barrier.

PAR-2 agonist peptides have been shown to significantly delay the recovery of epidermal barrier impermeability after acute barrier disruption in the skin of a mouse model.

These data show that KLK-5 is involved in the disruption of the barrier function observed in rosacea, in particular through its activation of PAR-2. In addition, the involvement of this proteolytic enzyme (or protease) in the activation of LL-37 confirms its major role in the inflammatory process that accompanies the manifestations of rosacea.

Therefore, KLK-5 is a preferential target for the treatment of rosacea and/or telangiectasia because the inhibition of its activity and/or the decrease in its expression may contribute to strengthening the barrier function, which limits the penetration of allergens, bacteria and irritants and, at the same time, reduce inflammation.

The targeting of KLK-5 by dermatological active ingredients has already been described. By way of example, document FR 3 022 139 describes a cosmetic composition comprising mineral salts of xanthan gum, a hydroalcoholic extract of ginseng and an extract of Ascophyllum nodosum, for its use in the treatment of rosacea thanks to its inhibitory activity of the enzymatic activity of KLK-5.

However, this cosmetic composition has the major drawback of containing extracts not titrated in active molecules and whose composition does not appear to be known or mastered.

Other conventional treatments involve giving the patient antibiotics for their anti-inflammatory effect. However, such treatments are photosensitizing (increasing the skin's sensitivity to UV rays) and require the use of effective sun protection. Local treatments (cream, gel or emulsion) are also known, optionally in combination with the oral administration of antibiotics. However, the downsides of these treatments are that they cause undesirable effects in the subject with rosacea, such as worsening of the redness or a burning sensation of the skin.

Another available treatment for rosacea is laser therapy to burst small vessels, selective photothermolysis, or welding of small vessels by photothermocoagulation. A major downside to this treatment is that it is expensive. In addition, it needs to be done outside of sunny periods.

Therefore, there remains an obvious need to develop a composition comprising dermatological active compounds which are safe for human topical use and which make it possible to carry out an effective long-term treatment of rosacea and/or telangiectasia through the inhibition of the overproduction of the KLK-5 protease.

DESCRIPTION OF THE INVENTION

The Applicant observed that, surprisingly, several dermatological active principles, which are perfectly safe and suitable for human cosmetic use, make it possible to overcome the drawbacks and meet the needs described above.

The invention aims, in general, to meet a real cosmetic need by moisturizing and soothing the skin, reducing feelings of discomfort and, ultimately, improving the appearance of the skin.

In particular, the invention aims to treat rosacea and/or telangiectasia in order to improve the appearance of the skin and reduce blemishes.

An aim of the invention is to provide a composition making it possible to decrease the cleavage of the hCAP 18 protein in LL-37, decrease the content of LL-37 in the skin, decrease the expression of the KLK-5 gene and/or the proteolytic activity of the KLK-5 enzyme and decrease the expression of the PAR-2 gene and/or the activity of PAR-2.

In particular, the Applicant observed that the dermatological active principles according to the invention make it possible to reduce the levels of production of KLK-5 and/or of expression of the KLK-5 protease gene and/or the proteolytic activity of KLK-5 and, therefore, the invention makes it possible to treat skin inflammation and/or reinforce the barrier function of the skin.

For the purposes of the invention, the term "dermatological active principle" is understood to mean a substance or a compound intended to be applied to the skin and which has biological and/or therapeutic properties which underlie a physiological effect.

The dermatological active principle should be distinguished from at least one excipient, present in the composition according to the invention.

For the purposes of the invention, the term "levels of KLK-5" is understood to mean the level of production of the KLK-5 protease, i.e., the content of KLK-5, and/or the level of expression of the KLK-5 protease gene and/or the activity of the KLK-5 protease.

For the purposes of the invention, the term "excipient" is understood to mean a substance other than the dermatological active principle which confers certain properties on the composition, in particular galenic and that of consistency and/or vectorization of the active principle.

Thus, and according to a first aspect, the invention relates to a composition comprising, as dermatological active principle, at least one polysaccharide selected from the group consisting of heteropolymers of glucose and trehalose; branched hydrogenated glucose homopolymers comprising α (1-4) and α (1-6) bonds and branched glucose homopolymers comprising α (1-4) and α (1-6) bonds, for use in the treatment of rosacea and/or telangiectasia.

In the remainder of the description, the term "composition according to the invention" also is understood to mean the composition according to the invention for its use for the treatment of rosacea and/or telangiectasia.

According to a particular embodiment, the glucose and trehalose heteropolymer according to the invention corresponds to the INCI designation maltooligosyl glucoside (or maltooligosyl glucoside (INCI)). In the remainder of the description, the term "maltooligosyl glucoside" is understood to mean the INCI designation maltooligosyl glucoside.

For the purposes of the invention, the glucose and trehalose heteropolymer, advantageously maltooligosyl glucoside, corresponds to a mixture of oligosaccharides consisting of one, two, three or four glucose residues linked to a trehalose residue.

According to a particular embodiment, the glucose and trehalose heteropolymer according to the invention, advantageously maltooligosyl glucoside (INCI), comprises maltotriosyl glucoside, i.e., an oligosaccharide consisting of three glucose residues linked to a residue of trehalose.

According to another particular embodiment, the glucose and trehalose heteropolymer according to the invention, advantageously maltooligosyl glucoside (INCI), is a mixture of several oligosaccharides comprising maltotriosyl glucoside in an amount of between 40% and 90% by weight of the total mixture of oligosaccharides (i.e., by weight of the total maltooligosyl glucoside), advantageously between 50% and 80%.

According to another particular embodiment, the glucose and trehalose heteropolymer according to the invention, advantageously maltooligosyl glucoside (INCI), comprises the combination of maltriosyl glucoside and maltotetrasyl glucoside, said combination representing between 10% and 40% by weight of the total mixture of oligosaccharides (i.e., by weight of the total maltooligosyl glucoside), preferably between 15% and 25%.

Advantageously, the glucose and trehalose heteropolymer according to the invention, advantageously maltooligosyl glucoside (INCI), further comprises maltotetraitol and maltotriiol.

The glucose and trehalose heteropolymer according to the invention, advantageously maltooligosyl glucoside (INCI), may be obtained by chemical synthesis or, preferably, by biotechnology.

According to a particular embodiment, the glucose and trehalose heteropolymer according to the invention, advantageously maltooligosyl glucoside, represents between 0.001% and 2% by weight of the composition, advantageously between 0.01% to 0.5%.

According to a particular embodiment, the branched hydrogenated glucose homopolymer comprising α (1-4) and α (1-6) bonds according to the invention corresponds to the INCI designation hydrogenated starch hydrolysate (or hydrogenated starch hydrolysate (INCI)). In the remainder of the description, the term "hydrogenated starch hydrolysate" is understood to mean the INCI designation hydrogenated starch hydrolysate.

The branched hydrogenated glucose homopolymer comprising α (1-4) and α (1-6) bonds according to the invention, advantageously hydrogenated starch hydrolysate (INCI), is obtained by controlled hydrogenation of partially digested vegetable starch. It may be a starch extracted from one or more plants, such as, for example, corn and/or potato. The hydrolysis may be carried out, for example, by enzymatic digestion or treatment with a weak acid while the hydrogenation may be carried out according to the methods known to a person skilled in the art in the field of the food industry, for example, incubation with hydrogen gas in the presence of metal catalysts.

According to a particular embodiment, the branched hydrogenated glucose homopolymer comprising α (1-4) and α (1-6) bonds, advantageously hydrogenated starch hydrolysate, represents between 0.001% and 2% by weight of the composition, advantageously between 0.01% and 0.5%.

According to a particular embodiment, the branched glucose homopolymer comprising α (1-4) and α (1-6) bonds according to the invention corresponds to the INCI designation glycogen (or glycogen (INCI)). In the remainder of the description, the term "glycogen" is understood to mean the INCI designation glycogen.

According to a particular embodiment, the branched glucose homopolymer comprising α (1-4) and α (1-6) bonds, advantageously glycogen, represents between 0.001% and 2% by weight of the composition, advantageously between 0.01% and 0.6%.

According to a particular embodiment, the branched glucose homopolymer comprising α (1-4) and α (1-6) bonds, advantageously glycogen, has a molecular weight of between 1 KDa and 10 KDa, advantageously between 4 and 6 KDa.

Glycogen is a branched glucose polysaccharide found in most organisms, particularly in humans. The branched glucose homopolymer comprising α (1-4) and α (1-6) bonds according to the invention, advantageously glycogen, may be obtained by chemical synthesis or, preferably, by biotechnology.

The branched glucose homopolymer comprising α (1-4) and α (1-6) bonds, advantageously glycogen, may be of animal or plant origin, for example, derived from corn or potato, or even.

Advantageously, the glycogen (INCI) according to the invention corresponds to glycogen the purity of which is 80%, or even 90%, preferably 95%, or even 99% or more, for example 100%. According to a particular embodiment, the branched glucose homopolymer comprising α (1-4) and α (1-6) bonds according to the invention corresponding to the INCI designation glycogen (INCI) is the raw material BIOGLYCOGEN® marketed by GLICO NUTRITION CO., LTD.

According to a preferred embodiment, the composition according to the invention comprises:
  at least one glucose and trehalose heteropolymer, advantageously representing between 0.001% and 2% by weight of the composition, preferably between 0.01% to 0.5%; and
  at least one branched hydrogenated glucose homopolymer comprising α-(1-4) and α-(1-6) bonds, advantageously representing between 0.001% and 2% by weight of the composition, preferably between 0.01% and 0.5%.

Advantageously, the composition according to the invention comprises maltooligosyl glucoside and hydrogenated starch hydrolysate.

According to a particular embodiment, the composition according to the invention comprises:
  at least one glucose and trehalose heteropolymer, advantageously representing between 0.001% and 2% by weight of the composition, preferably between 0.01% to 0.5%;
  at least one branched hydrogenated glucose homopolymer comprising α-(1-4) and α-(1-6) bonds, advantageously representing between 0.001% and 2% by weight of the composition, preferably between 0.01% and 0.5%; and at least one branched glucose homopolymer comprising α-(1-4) and α-(1-6) bonds, advantageously representing between 0.001% and 2% by weight of the composition, advantageously between 0.01% and 0, 6%.

Advantageously, the composition according to the invention comprises maltooligosyl glucoside, hydrogenated starch hydrolysate and glycogen.

According to a particular embodiment, the composition according to the invention comprises:
- at least one glucose and trehalose heteropolymer, advantageously representing between 0.001% and 2% by weight of the composition, preferably between 0.01% to 0.5%;
- at least one branched hydrogenated glucose homopolymer comprising α-(1-4) and α-(1-6) bonds, advantageously representing between 0.001% and 2% by weight of the composition, preferably between 0.01% and 0.5%; and eventually
- at least one branched glucose homopolymer comprising α-(1-4) and α-(1-6) bonds, advantageously representing between 0.001% and 2% by weight of the composition, advantageously between 0.01% and 0.6%; in addition, said composition has a weight ratio between the at least one glucose and trehalose heteropolymer and the at least one branched hydrogenated glucose homopolymer comprising α-(1-4) and α-(1-6) bonds, advantageously between the INCI maltooligosyl glucoside and the glycogen, between 3/1 and 1/3, preferably between 2/1 and 1/2.

According to a particular embodiment, the composition according to the invention is a cosmetic composition.

It emerges from the foregoing that the composition, advantageously cosmetic, according to the invention makes it possible to relieve the embarrassment and discomfort associated with rosacea and/or telangiectasia. In particular, the composition according to the invention reduces the intensity of redness, soothes (reduction of tightness and sensations of roughness) and moisturizes the skin. Thus, the present invention makes it possible to meet a real cosmetic need.

According to a particular embodiment, the composition according to the invention is free from probiotics.

For the purposes of the invention, the term "probiotics" is understood to mean living microorganisms which confer a benefit for the health of the host, when consumed in sufficient concentrations. They may interact with the host to improve immunity, intestinal homeostasis, stimulate metabolism, or reduce the risk of infection with opportunistic pathogens. Most bacterial probiotics belong to lactic acid bacteria. This group includes 10 genera, the best known of which are *Lactobacillus, Pediococcus, Lactococcus, Enterococcus, Streptococcus, Leuconostoc* and *Carnobacterium*.

Advantageously, the composition according to the invention is free from the following probiotics: *Lactobacillus casei, Lactobacillus acidophillus, Bacillus coagulans* and/or *Bifida* ferment lysate (INCI).

According to another embodiment, the composition according to the invention further comprises at least one UV filter. Filtration of UV light is known to improve the general condition of the skin, especially in individuals with rosacea and/or telangiectasia.

For the purposes of the invention, the term "UV filter" is understood to mean mineral or organic compounds (or chemical compounds) capable of filtering UV-A, UV-B and/or UV-C.

According to the invention, they may be mineral filters as well as chemical or organic filters.

The compositions according to the invention may contain one or more broad spectrum UV filters, i.e., compounds or mixtures which absorb UV-A, UV-B, UV-C and optionally visible light.

Among the broad spectrum organic filters, the filters corresponding to the following INCI designations may be used in the context of the invention: tris biphenyl triazine, bis ethylhexyloxyphenol methoxyphenyl triazine, methylene bis-benzotriazolyl tetramethylbutylphenol. By way of example, these are marketed by BASF under the names TINOSORB S®/TINOSORB AQUA®, TINOSORB A2B®, TINOSORB M®, respectively. Another example of a broad spectrum filter suitable for the composition according to the invention meets the INCI designation diethylhexyl butamido triazone, for example sold by SIGMA 3V under the name UVASORB HEB®.

Thus, and in a particular embodiment, the composition according to the invention comprises at least one filter selected from the following group of compounds identified by their INCI designation: tris biphenyl triazine, bis ethylhexyloxyphenol methoxyphenyl triazine, and methylene bis-benzotriazolyl tetramethylbutylphenol, diethylhexyl butamido triazone, or mixtures thereof.

Advantageously, the composition comprises the bis-ethylhexyloxyphenol methoxyphenyl triazine filter.

According to another embodiment, instead of, or in addition to, the broad spectrum filter(s), the composition contains at least one organic and/or inorganic UV-A and/or UV-B filter, which may be present in aqueous (lipophilic) and/or oily (liposoluble) phase.

Thus, and by way of example, the composition according to the invention may contain liposoluble UV-B filters capable of contributing to the stabilization or to the solubilization of broad spectrum filters or reciprocally stabilizing, and thereby increasing, the sun protection factor (SPF).

Advantageously, such filters correspond to the following INCI designations: homosalate, octocrylene, ethylhexyl salicylate, ethylhexyl triazone.

In a preferred embodiment, the composition according to the invention comprises ethylhexyl triazone, marketed by BASF under the name UVINUL T150®.

In another embodiment, the liposoluble UV-B filter is α-(trimethylsilyl)-ω-(trimethylsilyloxy)poly[oxy(dimethyl)silylene]-co-[oxy(methyl)(2-{4-[2,2-bis(ethoxycarbonyl)vinyl]phenoxy}-1-methyleneethyl)silylene]-co-[oxy(methyl)(2-(4-[2,2-bis(ethoxycarbonyl)vinyl]phenoxy)prop-1-enyl)silylene], a silicone polymer capable of filtering in UV-B. This filter corresponds, for example, to the cosmetic raw material Parsol SLX®, marketed by DSM under the INCI designation polysilicone-15.

In a particular embodiment, the composition according to the invention comprises at least one UV-B filter selected from the following group of compounds identified by their INCI designation: homosalate, ethylhexyl salicylate, ethylhexyl triazone, polysilicone-15, or mixtures thereof.

In a particular embodiment, the composition is free from the following filters: 4-methylbenzylidene camphor, benzophenone-2, benzophenone-3, ethylhexyl methoxycinnamate, octocrylene.

In an advantageous embodiment, the composition according to the invention comprises at least one UV-A filter, in order to ensure complete filtration of the harmful part of the solar spectrum.

Advantageous UV-A filters within the meaning of the present invention are butyl methoxydibenzoylmethane (INCI) and diethylamino hydroxybenzoyl hexyl benzoate (INCI), corresponding respectively to the raw materials Parsol 1789® marketed by DSM and UVINUL® A+marketed by BASF.

In a particular embodiment, the UV-A filter is bis-(diethylaminohydroxybenzoyl benzoyl) piperazine (INCI) (CAS number 919803-06-8), corresponding, for example, to the raw material C1332® marketed by BASF.

Thus, and in a preferred embodiment, the composition according to the invention comprises at least one filter selected from the following group of compounds identified by their INCI designation: butyl methoxydibenzoylmethane, diethylamino hydroxybenzoyl hexyl benzoate, bis-(diethylaminohydroxybenzoyl benzoyl) piperazine, or their mixtures.

Other advantageous UV filters within the meaning of the present invention are hydrosoluble filters, such as for example:
- the filter corresponding to the INCI designation disodium phenyl dibenzimidazole tetrasulfonate, in particular available under the name Neo Heliopan® AP (Symrise);
- the filter corresponding to the INCI designation phenylbenzimidazole sulfonic acid, in particular available under the name Neo Heliopan® hydro (Symrise), preferably in combination with a basic amino acid, advantageously arginine. In practice, the basic amino acid represents between 0.5 and 2% by weight of the composition, preferably between 1 and 1.5% by weight of the composition. In a preferred embodiment, the composition according to the invention comprises at least one hydrosoluble filter selected from the following group of compounds identified by their INCI designation: disodium phenyl dibenzimidazole tetrasulfonate, phenylbenzimidazole sulfonic acid, or mixtures thereof.

Advantageously, inorganic mineral filters, or mineral screens, are metal oxides and/or other compounds which are poorly soluble or insoluble in water, in particular titanium ($TiO_2$), zinc (ZnO), iron ($Fe_2O_3$), zirconium ($ZrO_2$), silicon ($SiO_2$), manganese (for example, MnO), aluminum ($Al_2O_3$), or cerium ($Ce_2O_3$) oxides.

According to a particular embodiment, the inorganic mineral filters may be used in the form of an oily or aqueous predispersion available on the market. These predispersions may advantageously be added with dispersing auxiliaries and/or solubilization mediators.

Inorganic mineral filters may also be surface-treated or encapsulated in order to give them a hydrophilic, amphiphilic or hydrophobic character. This surface treatment may consist of the inorganic filters being provided with a thin hydrophilic and/or hydrophobic inorganic and/or organic film.

In a preferred embodiment, the composition according to the invention comprises at least one mineral screen selected from the following group of compounds identified by their INCI designation: Zinc oxide, Titanium dioxide, or mixtures thereof.

The lists of UV filters cited which may be used within the meaning of the present invention are, of course, given by way of indication and not by way of limitation.

Advantageously, the UV filters as described above, present in the composition according to the invention, represent from 0.1% to 30% by weight of the composition, advantageously between 0.5% and 20%, even more advantageously between 1% and 15%.

According to a particular embodiment, the composition according to the invention has a sun protection factor (SPF) greater than or equal to 10, preferably greater than or equal to 20, advantageously greater than or equal to 30, even more advantageously greater than or equal to 50.

According to a preferred embodiment, the composition according to the invention comprises a UV-A/UV-B protection ratio equal to or greater than 1/3.

The sunscreen composition according to the invention comprises at least one sunscreen solubilizer selected from the following group of compounds identified by their INCI designation: caprylyl caprylate/caprate, dibutyl adipate, dicaprylyl carbonate, diisopropyl sebacate, dicaprylyl ether, coco-caprylate, C12-15 alkyl benzoate, propylheptyl caprylate and butylene glycol dicaprylate/dicaprate. These solubilizers are available on the market from several suppliers. By way of example, the following raw materials may be used in the composition according to the invention:
- Several raw materials from the CETIOL® range marketed by BASF, in particular CETIOL® RLF, CETIOL® B, CETIOL® CC, CETIOL® 0, CETIOL® C5, CETIOL® AB, CETIOL® SENSOFT corresponding respectively to the INCI designations caprylyl caprylate/caprate, dibutyl adipate, dicaprylyl carbonate, dicaprylyl ether, coco-caprylate, C12-15 alkyl benzoate, propylheptyl caprylate;
- DUB DIS marketed by STEARINE DUBOIS corresponding to the INCI designation diisopropyl sebacate;
- MIGLYOL® 8810 marketed by 101 Oleo GmbH corresponding to the INCI designation butylene glycol dicaprylate/dicaprate.

In a preferred embodiment, the composition according to the invention comprises at least four solubilizers selected from the following group of compounds identified by their INCI designation: caprylyl caprylate/caprate, dibutyl adipate, dicaprylyl carbonate, diisopropyl sebacate, dicaprylyl ether, coco-caprylate, C12-15 alkyl benzoate, propylheptyl caprylate and butylene glycol dicaprylate/dicaprate.

In a particular embodiment, the composition according to the invention comprises the solubilizers corresponding to the INCI designations dibutyl adipate, dicaprylyl carbonate, diisopropyl sebacate. In a preferred embodiment, the composition according to the invention further comprises at least one other solubilizer selected from the following group of compounds identified by their INCI designation: propylheptyl caprylate, dicaprylyl ether, coco-caprylate, C12-15 alkyl benzoate, caprylyl caprylate/caprate. Advantageously, it is propylheptyl caprylate.

According to a preferred embodiment, the total weight of the solubilizers as defined above represent between 5% and 80% by weight of the total composition, advantageously between 10% and 70%, even more advantageously between 15 and 60%.

The composition according to the invention may also comprise an SPF "booster", i.e., an agent for enhancing the sun protection factor, and/or a light stabilizer, i.e., an ingredient which makes it possible to increase the SPF or light stabilize the filters, such an ingredient not itself being considered a sun filter. Examples include the following:
- butyloctyl salicylate (INCI), a light stabilizer advantageously representing between 0.01% and 10% by weight of the composition, even more advantageously between 0.1% and 2%. This raw material is, for example, marketed by HALLSTAR under the name Hallbrite® BHB;
- benzotriazolyl dodecyl p-cresol (INCI), a light stabilizer advantageously representing between 0.01% and 10% by weight of the composition, even more advantageously between 0.1% and 2%. This raw material is, for example, marketed by BASF under the name TINOGARD® TL;

pongamol (INCI), a plant molecule which absorbs UV-A, advantageously representing between 0.5 and 2% by weight of the composition, even more advantageously of the order of 1%. By way of example, the raw material Pongamia Extract marketed by GIVAUDAN may be used in the context of the present invention;

ethylhexyl methoxycrylene (INCI), light stabilizer, solubilizer and "booster" of SPF advantageously representing between 1% and 5% by weight of the composition. The SolaStay® S1 raw material marketed by HALLSTAR may be used in the context of the present invention;

a styrene acrylate copolymer (INCI: styrene/acrylate copolymer), preferably representing between 1% and 10% by weight of the composition according to the invention. The raw materials SunSpheres® H53 and SunSpheres® PGL Polymer, marketed by DOW CHEMICALS, may be used within the framework of the present invention;

diethylhexyl syringylidene malonate (INCI), advantageously representing between 1% and 10% by weight of the composition. The raw material OXYNET® ST, marketed by MERCK, may be used in the context of the present invention;

a water-dispersible polyester, corresponding to the INCI designations polyester-5 (and) Sodium silicoaluminate, advantageously representing between 1% and 10% by weight of the composition, in particular the EASTMANN AQTM38S Polymer marketed by SAFIC-ALCAN;

an acrylate copolymer having a glass transition temperature of −5° C. to −15° C. as measured by differential scanning calorimetry, said copolymer advantageously representing between 1% and 10% by weight of the composition. For example, a polymer corresponding to the INCI designation Acrylate copolymer, such as the raw material EPITEX 66, marketed by DOW CHEMICALS, may be used in the context of the present invention.

In a particular embodiment, the composition according to the invention also comprises one or more substances capable of filtering visible light, in particular blue light. By way of example, the compounds described in document EP 1 484 051 may be used to ensure filtration of blue light.

According to another aspect of the invention, the compositions according to the invention are formulated from an aqueous base having a defined composition and containing in particular calcium chloride; potassium chloride; potassium phosphate; magnesium sulfate; sodium chloride; sodium hydrogencarbonate; sodium hydrogen phosphate; sodium citrate; citric acid; carnosine and hypotaurine (2-aminoethanesulfinic acid).

Preferably, said aqueous base comprises:
from 0.000001% to 0.1% by weight of the total aqueous base of calcium chloride, advantageously from 0.0001% to 0.1%;
from 0.0001% to 0.1% by weight of the total aqueous base of potassium chloride, advantageously from 0.001% to 0.1%;
from 0.00001% to 0.1% by weight of the total aqueous potassium phosphate base, advantageously from 0.0001% to 0.1%;
from 0.0001% to 0.1% by weight of the total aqueous base of magnesium sulfate, advantageously from 0.001% to 0.1%;
from 0.001 to 4% by weight of the total aqueous sodium chloride base, advantageously from 0.1 to 4%;
from 0.0001 to 0.1% by weight of the total aqueous base of sodium hydrogencarbonate;
from 0.0001% to 0.1% by weight of the total aqueous base of sodium hydrogen phosphate;
from 0.0001% to 1% by weight of the total aqueous citric acid base, advantageously from 0.001% to 1%;
from 0.001% to 1% by weight of the total aqueous base of sodium citrate;
from 0.0001% to 1% by weight of the total aqueous carnosine base, advantageously from 0.001% to 1%;
from 0.0001 to 1% by weight of the total of the aqueous base of 2-aminoethanesulfinic acid, preferably from 0.001 to 1%.

In a particular embodiment, the composition according to the invention also contains active ingredients capable of improving skin hydration.

In a particular embodiment, the advantageously cosmetic composition according to the invention further comprises an apple seed extract, optionally supplemented with vitamin B3 (niacinamide or vitamin PP) or its derivatives. The apple seed extract (*Pyrus malus*) increases the synthesis of several aquaporins. Aquaporins are proteins that play a key role in the skin's hydration balance.

Vitamin PP and its derivatives act by stimulating the activity of serine palmitoyl transferase, an enzyme involved in the synthesis of sphingosine, a precursor molecule of ceramides, and thereby improve the barrier function of the skin and fight dry skin.

Preferably, the apple seed extract is an extract of lipophilic nature. In practice, the cosmetic raw material EDERLINE S, corresponding to the INCI designation Hexyldecanol & butylene glycol & *Pyrus malus* (apple) seed extract, or the raw material EDERLINE LS, corresponding to the INCI designation hexyldecanol & *Pyrus malus* (apple) seed extract & *Brassica campestris* (rapeseed) sterols & tocopherol, may be used as a source of apple seed extract. As for the raw material niacinamide, it is marketed by QUIMICA MASSO and corresponds to the INCI designation niacinamide.

Advantageously, the composition according to the invention comprises from 0.001% to 1% of *Pyrus malus* plant extract and/or from 0.001% to 10% of niacinamide by weight of the total composition.

In another embodiment, the advantageously cosmetic composition according to the invention further comprises an extract of the *Imperata cylindrica* plant (*I. cylindrica*), preferably a root extract, advantageously titrated in aquaporins. Indeed, the incorporation of extracts of *Imperata cylindrica* in the composition comprising the composition according to the invention makes it possible to improve the hydration of the stratum corneum.

In practice, the MOIST 24 PH raw material corresponding to the INCI designation *I. cylindrica* root extract & water & glycerin & PEG-8 & carbomer & phenoxyethanol & sodium citrate & potassium sorbate & citric acid and marketed by SEDERMA may be used within the scope of the present invention. Advantageously, the composition according to the invention comprises between 0.001% and 1% by weight of said composition of *I. cylindrica* plant extract, preferably between 0.01% and 0.1%.

In another embodiment, the advantageously cosmetic composition according to the invention further comprises a bioactive system combining, on the one hand, a stable form in aqueous solution of a nucleotide selected from ATP (adenosine triphosphate), Gp4G (diguanosine tetraphosphate) and Ap4A (diadenosine tetraphosphate); and, on the other hand, at least one biomimetic peptide comprising at most six amino acids, mimicking a skin polypeptide or a skin protein, or an agonist or antagonist biomolecule of said peptide or of said protein. In practice, the combination of these active ingredients catalyzes the metabolic activity of skin cells while obtaining a dermocosmetic or therapeutic effect through the use of biomimetic peptides. These may be selected in order to obtain the desired effect, for example, that of inhibiting irritations of neurogenic origin, a depigmenting activity, an effect of inhibiting any intolerance or sensitization, etc.

In practice, in the bioactive system according to the invention, the nucleotide represents at most 10% by weight of the composition, preferably between 0.001% and 5%; and the biomimetic peptide represents between 0.001% to 1% by weight of the composition.

According to another embodiment, the composition according to the invention may also comprise an extract of the bacterium *Arthrobacter agilis*, in particular an extract rich in carotenoids. Thus, the raw material corresponding to the INCI designation *micrococcus* lysate marketed by GREENTECH may be used within the framework of the present invention. Advantageously, the composition according to the invention comprises between 0.00001% and 0.1% by weight of the composition, preferably between 0.0001% and 0.001% of such a dry extract.

According to another embodiment, the composition according to the invention further comprises other components which may contribute to internal protection by an action which may consist of protecting the DNA, decreasing the immunosuppression induced by UV radiation, an anti-free radical action or a combined effect of these actions.

The protective action of a preparation according to the invention against oxidative stress or against the effect of free radicals can be further improved if it also comprises one or more antioxidants, easily selected by a person skilled in the art, for example from the following list: totarol, magnolol, honokiol, amino acids and their derivatives, peptides and their derivatives (for example anserine, hypotaurine, taurine), carotenoids, carotenes (α-carotene, β-carotene, lycopene) and their derivatives, chlorogenic acid and its derivatives, lipoic acid and its derivatives (dihydrolipoic acid), aurothioglucose, propylthiouracil and other thiols (thioredoxin, glutathione, cysteine, cystine, cystamine and their glycosyl, N-acetyl, methyl, ethyl, propyl, amyl, butyl and lauryl, palmitoyl, oleyl, γ-linoleic, cholesteryl and glyceryl esters as well as salts thereof, thiodipropionate dilauryl, distearyl thiodipropionate, thiodipropionic acid and its derivatives, sulfoximine compounds (buthionine sulfoximine, homocysteine sulfoximine, buthionine sulfones, penta-, hexa- and heptathionine sulfoximine), chelating agents (such as α-hydroxygras acids, palmitic acid, phytic acid, lactoferrin), α-hydroxy acids (such as citric, lactic, or malic acid), humic acid, bile acid, bilirubin, biliverdin, pentasodium tetramethylene phosphonate ethylenediamine and its derivatives, unsaturated fatty acids and their derivatives, vitamin A and its derivatives (vitamin A palmitate), coniferyl benzoate, rutinic acid and its derivatives, α-glycosyl rutin, ferulic acid and its derivatives, furfurylideneglucitol, butylhydroxytoluene, butylhydroxyanisole, nordihydroguaiaretic acid, trihydroxybutyrophenone, quercetin, uric acid and its derivatives, mannose and its derivatives, selenium and its derivatives (selenomethionine), stilbenes and their derivatives (stilbene oxide, trans-stilbene oxide).

In a particular embodiment, the composition according to the invention also contains glycyrrhetinic acid, a derivative or a salt of this acid, used as a soothing agent (anti-inflammatory agent) and representing between 0.01% and 2% by weight of the composition, preferably between 0.1% and 1%.

According to another embodiment of the invention, the advantageously cosmetic composition comprises at least one, or even all of the following constituents exerting a biological activity in vivo on the cells of the skin, lips, hair and/or mucous membranes subjected to UV-A and/or UV-B radiation, respectively:
  an anti-free radical preserving cell structures, such as, for example, vitamin E and/or its liposoluble or hydrosoluble derivatives, in particular tocotrienol and/or tocopherol, advantageously representing between 0.001% and 10% by weight of the composition, again more preferably between 0.02% and 2%, preferably 0.04%; —an agent limiting immunosuppression, such as, for example, vitamin PP, advantageously representing between 0.001% and 1% by weight of the composition, preferably between 0.01% and 0.3%;
  a protective agent for the p53 protein, such as, for example, epigallocatechin gallate (EGCG), advantageously representing between 0.001% and 0.1% by weight of the composition, preferably between 0.005% and 0.05%.

In a particular embodiment of the invention, the advantageously cosmetic composition according to the invention also contains active ingredients capable of stimulating the proliferation of skin cells, advantageously fibroblasts and/or keratinocytes, preferably human or animal fibroblasts. In particular, and according to this embodiment, the cosmetic composition according to the invention further comprises:
  an α-lipoic acid or a salt thereof;
  a vitamin C derivative selected from ethyl ascorbic acid and sodium ascorbate or a mixture thereof; and
  a hyaluronic acid, the molecular weight (Mw) of which is advantageously between 0.5 and 15 kDa, preferably 0.5 and 10 kDa.

Advantageously, the α-lipoic acid or one of its salts represents less than 0.1%, advantageously less than 0.01% by weight of the cell culture medium, preferably between 0.001% and 0.0005%.

Advantageously, the derivative of vitamin C selected from ethyl ascorbic acid and sodium ascorbate or their mixture, advantageously ethyl ascorbic acid, preferably 3-0 ethyl ether of ascorbic acid, represents between 0.001% and 10% by weight of the cell culture medium, advantageously between 0.01% and 5%, preferably between 0.1% and 1%.

Advantageously, hyaluronic acid, whose molecular weight (Mw) is advantageously between 0.5 and 15 kDa, preferably 0.5 and 10 kDa, represents between 0.001% and 10% by weight of the cell culture medium, advantageously between 0.01% and 5%, preferably between 0.1% and 1%. The composition according to the invention may also further comprise soy and/or wheat peptide extracts.

In practice, the peptide extracts coming from soybeans and wheat seeds are obtained from an enzymatic hydrolysis of said seeds by means of peptidases which makes it possible to recover peptides with an average size of 700 Daltons. Preferably, the soy peptide extract is the extract identified under CAS number 68607-88-5 just as the wheat peptide extract is the extract identified under CAS number 70084-

87-6. The wheat and soy extracts may correspond to the INCI designations hydrolyzed wheat protein and hydrolyzed soy protein, respectively.

In a particular embodiment, the soy and wheat peptide extracts are used together, for example in a weight ratio of between 80/20 and 20/80 respectively, advantageously between 70/30 and 30/70, preferably equal at 60/40.

In an advantageous embodiment, the soy and/or wheat peptide extracts are free from synthetic tripeptides GHK (glycyl-histidyl-lysine; INCI: Tripeptide-1). In practice, the soy and/or wheat peptide extracts represent between 0.01% and 20% by weight of the composition, advantageously between 0.1% and 10%, preferably between 0.2% and 0.7%.

The composition according to the invention is advantageously formulated to be cosmetically acceptable, i.e., compatible with the skin, mucous membranes, hair and scalp. Preferably, the composition of the invention is a composition for skin application or for topical use.

The term "composition for cutaneous application" or "for topical use" is understood to mean a composition compatible with application to the skin, mucous membranes, hair and/or scalp, preferably human skin.

The composition of the invention may be in any galenic form suitable for topical application, in particular in the form of an aqueous, hydroalcoholic, organic or oily solution; suspension or dispersion in solvents or fatty substances, of the lotion or serum type; in the form of a vesicular dispersion; in the form of a water-in-oil (W/O), oil-in-water (O/W) or multiple emulsion such as a water-in-oil-in-water (W/O/W) emulsion. The emulsion may be thicker or thinner and is in the form of cream or milk; the composition of the invention may also be in the form of an ointment, a gel, a solid stick, pasty or solid anhydrous products, a foam, in particular an aerosol, a two-phase composition or else a sprayable composition.

The dosage form of the composition and its method of preparation, and therefore the excipients suitable for the composition of the invention, may be selected by a person skilled in the art on the basis of their general knowledge depending on the type of composition sought.

In particular, and according to a preferred embodiment, the compositions according to the present invention comprise an advantageously colored particle with a blurring effect or a mixture of several particles with a blurring effect. These particles with a blurring effect are also referred to as "particles with a soft-focus effect" or even "particles with a blur effect".

According to the invention, the term "particle with a blurring effect" is understood to mean a particle, advantageously colored, intended to give more transparency to the complexion and a blur effect. In particular, the particle with a blurring effect enables the composition which contains it to attenuate the skin microrelief by optical effect and, in particular, skin defects such as spots, wrinkles, fine lines.

Several particles with a soft-focus or blurring effect are available on the market; by way of example, mention may be made of the raw materials of the Ronasphere (MERCK) range based on silica substrate, in particular RONASPHERE FLAWLESS, as well as several raw materials marketed by JGC-C & C (Coverleaf range based on sericite substrate or sericite/talc), Nihon Koken (Relief Color range, Silséem based on mica/silica substrate), or Miyoshi Kasei (PC-Bail range based on silica substrate).

According to a preferred embodiment, the compositions of the invention comprise, as particle with a blurring effect, a composite particle comprising sericite, brown iron oxide, titanium dioxide and silica. Such particles are marketed, for example, under the references COVERLEAF NS or JS or MF by CHEMICALS AND CATALYSTS.

The colored particle with a blurring effect may have a structure which may, for example, be of the silica microsphere type containing iron oxide, such as that sold by MIYOSHI under the reference PC BALL PC-LL-100 P, this pigment consisting of silica microspheres containing yellow iron oxide. According to a preferred embodiment, a composite particle having a structure of the sericite/brown iron oxide/titanium dioxide/silica type, such as that sold under the reference COVERLEAF MF by CHEMICALS AND CATALYSTS, is used as a colored particle with a blurring effect.

According to another embodiment, the raw material GRANPOWDER USQ marketed by Grant Industries Inc. and corresponding to the INCI designations polymethylsilsesquioxane (and) HDI/Trimethylol Hexyllactone Crosspolymer may be used as a particle with a blurring effect.

Alternatively, the raw material COVAMED PMMA 2 MUSI marketed by SENSIENT COSMETICS TECHNOLOGY corresponding to the INCI designations methyl methacrylate crosspolymer and silica may be used as a particle with a blurring effect.

According to an alternative embodiment, the D-400 raw material marketed by TOCHI corresponding to the INCI designations HDI/trimethylol hexyllactone crosspolymer and silica may be used as a colored particle with a blurring effect.

According to yet another embodiment, the raw material KSP-100 marketed by SHINETSU corresponding to the INCI designation vinyl dimethicone/methicone silsesquioxane crosspolymer may be used as a particle with a blurring effect.

Preferably, the compositions according to the invention comprise from 0.5% to 20%, advantageously from 1% to 10%, even more advantageously from 1% to 5% by weight of particles with a blurring effect by weight of the composition.

According to a particular embodiment, the composition according to the invention comprises any fatty substance usually used in cosmetics. Mention may in particular be made of silicone fatty substances such as silicone oils, gums and waxes, as well as non-silicone fatty substances such as oils and waxes of plant, mineral, animal and/or synthetic origin. Oils may be volatile or non-volatile. Mention may also be made of hydrocarbons, synthetic esters and ethers, fatty alcohols and fatty acids. The composition may also comprise an aqueous medium, a hydroalcoholic medium containing an alcohol such as ethanol or isopropanol, or an organic medium comprising usual organic solvents such as C1-6 alcohols, in particular ethanol and isopropanol, glycols such as propylene glycol, ketones.

The composition may comprise at least one conventional emulsifier, selected from amphoteric, anionic, cationic or nonionic emulsifiers, used alone or as a mixture.

It may also include adjuvants customary in the field under consideration, such as hydrophilic or lipophilic thickeners or gelling agents, hydrophilic or lipophilic additives, active ingredients, in particular cosmetic agents, preservatives, antioxidants, perfumes, fillers, pigments, absorbers, odor, dyes, moisturizers (glycerin), vitamins, essential fatty acids, liposoluble polymers in particular hydrocarbon-based, opacifiers, stabilizers, sequestering agents, conditioners and propellants.

Of course, a person skilled in the art will ensure to choose this or these optional adjuvants or additional excipients, and/or their amount, in such a way that the advantageous properties of the composition according to the invention are not, or substantially not, altered by the proposed addition.

It may be particularly advantageous to formulate the composition of the invention so that it is sprayable. This can be achieved, for example, by formulating specific emulsions comprising particular combinations of excipients.

According to another aspect, the invention relates to a cosmetic treatment process consisting in applying a composition as defined above to the skin.

The compositions used in this treatment process are those described above.

Advantageously, and in relation to these various applications, the composition of the invention is applied or administered topically.

The manner in which the invention can be implemented and the advantages which result therefrom will emerge more clearly from the exemplary embodiments which follow, given by way of indication and without limitation, in support of the appended figures.

Figure 1:
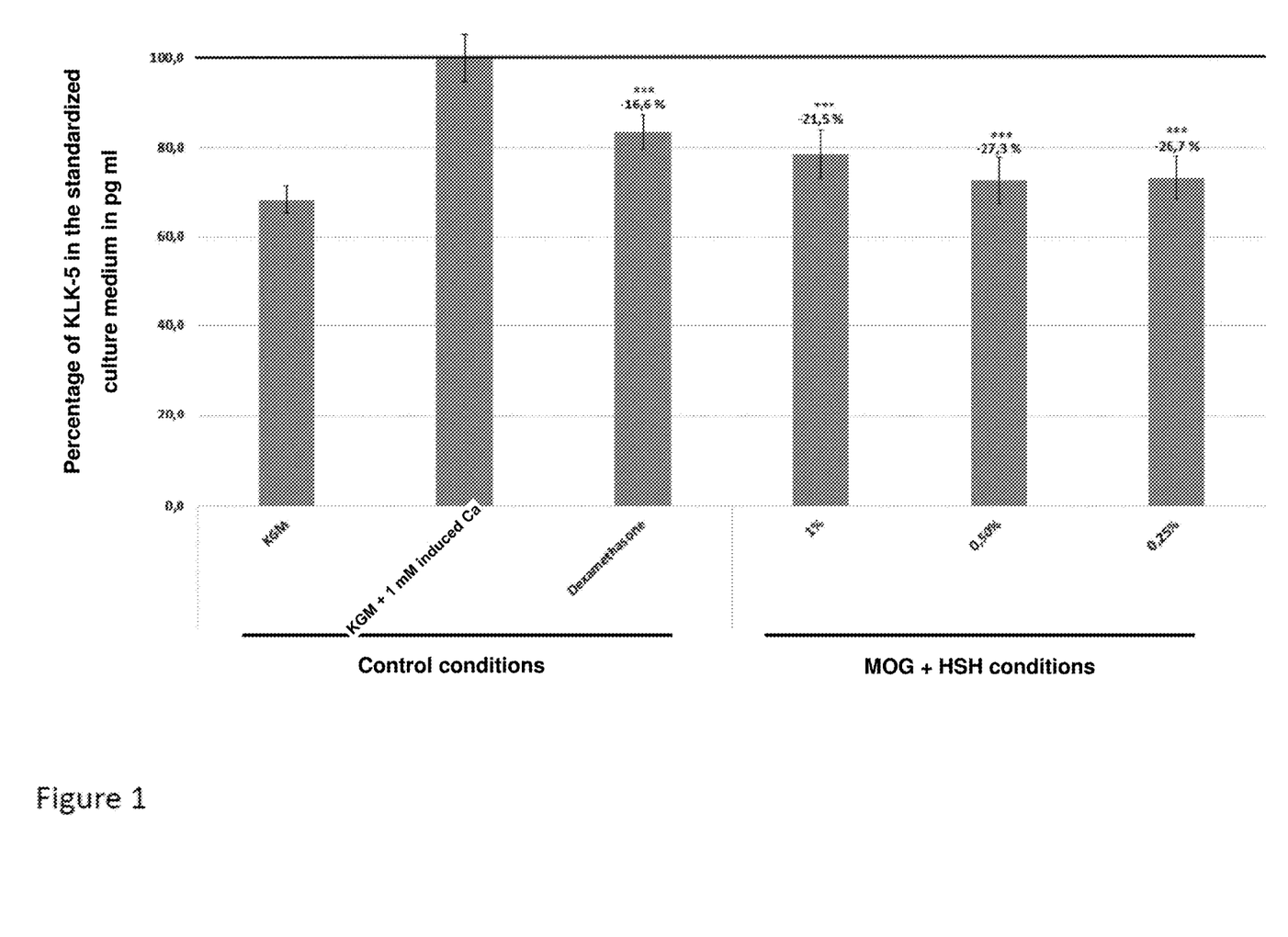
FIG. 1 shows the effect of the combination of maltooligosyl glucoside polysaccharides (INCI; hereinafter referred to as MOG) and hydrogenated starch hydrolysate (INCI; hereinafter referred to as HSH) on the inhibition of the synthesis of KLK-5 secreted by normal human keratinocytes (NHK) after 48 hours of incubation. The positive control selected is dexamethasone at 1 µM. The results are expressed as a percentage of expression normalized to cell viability. They represent the data obtained on 1 experiment carried out in triplicate.

FIG. 1 shows the effect of the combination of maltooligosyl glucoside (MOG) and hydrogenated starch hydrolysate (HSH) polysaccharides on the inhibition of the synthesis of KLK5 secreted by NHKs after 48 hours of incubation. The positive control selected is dexamethasone at 1 µM. The results are expressed as a percentage of expression normalized to cell viability. They represent the data obtained on 1 experiment carried out in triplicate.

EXEMPLARY EMBODIMENTS

Example 1: Cosmetic Composition within the Meaning of the Invention—O/W Emulsion—Fluid Cream A composition according to the invention is described in Table 1.

| Compound (INCI designation) | Weight (in %) |
|---|---|
| Water | 77.165 |
| Hydrogenated polydecene | 10.00 |
| Glycerin | 5.00 |
| Cetearyl alcohol | 2.40 |
| Phenoxyethanol | 1.015 |
| PEG-100 stearate | 1.00 |
| Glyceryl stearate | 1.00 |
| 1,2-hexanediol | 1.00 |
| Cetearyl glucoside | 0.60 |
| Maltooligosyl glucoside | 0.235 |
| Disodium EDTA | 0.20 |
| Caprylyl glycol | 0.15 |
| Hydrogenated starch hydrolysate | 0.135 |
| Carbomer | 0.10 |

Example 2: Cosmetic Composition within the Meaning of the Invention—O/W Emulsion—Rich Balm A composition according to the invention is described in Table 2.

| Compound (INCI designation) | Weight (in %) |
|---|---|
| Water | 64.51 |
| Caprylic/capric triglyceride | 9.00 |
| Glycerin | 8.00 |
| *Olea europaea* (olive) fruit oil | 7.00 |

-continued

| Compound (INCI designation) | Weight (in %) |
|---|---|
| *Mangifero indica* (mango) seed butter | 3.00 |
| Sucrose stearate | 2.50 |
| Sucrose distearate | 2.50 |
| C10-C18 triglycerides | 2.00 |
| Glycogen | 0.30 |
| Xanthan gum | 0.30 |
| Potassium sorbate | 0.20 |
| Sodium benzoate | 0.20 |
| Sodium citrate | 0.20 |
| Lactic acid | 0.19 |
| Fragrance | 0.1 |

Example 3: Actions of the Active Ingredients According to the Invention on the Cellular Synthesis of KLK-5 in an Environment Mimicking Rosacea 1—Purpose of the Study The purpose of the study is to demonstrate the effect of active ingredients on the inhibition of the synthesis of the KLK5 protein by normal human keratinocytes (NHK) in an environment mimicking rosacea.

2—Materials and Methods 2.1—Cell Culture

NHKs originating from LONZA (France) were used in this study.

The culture conditions are as follows:

Cell type: NHK donor PP12
Culture medium: KBM+Lonza supplements=KGM
Seeding density: 15,000 cells/well in 96-well plates with 100 µl of medium.

The conditions for induction of the synthesis of KLK-5 are as follows:

Presence of 1 mM of calcium
Inducer mix: (see Table 1) IL-17 at 10 ng/ml+Vit. D at $10^{-7}$ mol/L
Processing time: 48 hours
Positive control of induced KLK5 inhibition: Dexamethasone at 1 µM The following KLK-5 inducers listed in Table 3 were used in the study:

| Inducer | Supplier | Concentration tested | Stock solution |
|---|---|---|---|
| IL-17 | R&D Systems | 10 ng/ml | 50 µg/ml |
| Vit D | Sigma | $10^{-7}$M | 0.418 g/L |

2.2—Determination of KLK-5 in the Culture Supernatants by ELISA

The quantification of KLK-5 in the supernatants is carried out using an Enzyme Linked Immunosorbent Assay (ELISA) (Ref: DY8459-05, R&D Systems, France) with the reagents recommended by the manufacturer (DuoSet Ancillary Reagent Kit 2, Ref: DY008, R&D Systems, France) and used according to the manufacturer's instructions.

The optical density (OD) is read with a spectrophotometer at 450 nm. The concentration of KLK-5 is calculated from the standard range (15.6 to 1000 pg/ml) established with the recombinant human protein of KLK-5.

A dilution of the supernatants to 1/50th is mandatory so that the samples are not out of range. The results are expressed in pg/ml of KLK-5 per well. On the cell layer, a viability test with MTT ((3-4,5-dimethylthiazol-2-yl)-2,5-diphenyl tetrazolium bromide) is carried out. KLK-5 assays are only run if the cell viability is greater than 80%, and are related to this cell viability value.

2.3—MTT Cell Viability Test

MTT is a soluble yellow dye which is metabolized by mitochondrial enzymes (succinate dehydrogenase) into a dark blue compound: formazan. The formazan crystals are then dissolved in DMSO then the optical density is measured spectrophotometrically at 540 nm. This method was established by Mosmann (1983), and the protocol was subsequently modified by Denizot et al. (1986).

2.4—Experimental Protocol

The NHKs are inoculated in KGM medium and incubated for 24 hours at 37° C. in the presence of 5% $CO_2$ before treatment with the compounds under study in KGM and 1 mM of $CaCl_2$). After 1 h of incubation with the active ingredients, induction of KLK-5 is carried out with the combination of IL-17 at 10 ng/ml+Vit. D at 10-7 mol/L. The NHKs are incubated for 48 hours at 37° C. in the presence of 5% $CO_2$; subsequently, the supernatants are recovered and the KLK-5 ELISA assays as well as the MTT cell viability test are carried out.

2.5—Active Ingredients Under Study

The following polysaccharides listed in Table 4 were tested:

| Active ingredients (abbreviation) | INCI Name |
| --- | --- |
| MG-60 (MOG + HSH) | Maltooligosyl glucoside & hydrogenated starch hydrolysate |
| Bioglycogen (GG) | Glycogen |

The active ingredients selected are hydrosoluble.

The amount of solvent in the active ingredients was adjusted to 0.1% ETOH: indeed, there is 0.1% ETOH in the Vit. D inducer. The results of the active ingredients are compared with the solvent controls.

2.6—Statistical Analyzes

The data were collected from independent experiments carried out in triplicate. Quantitative analyzes are expressed as the mean±standard deviation. Statistical significance is determined by a Student test. The differences are considered statistically significant from p<0.05. (NS: p>0.05; *:1.30.05; :p0.01; *:p0.001).

3—Results and Conclusion

Figure 2:
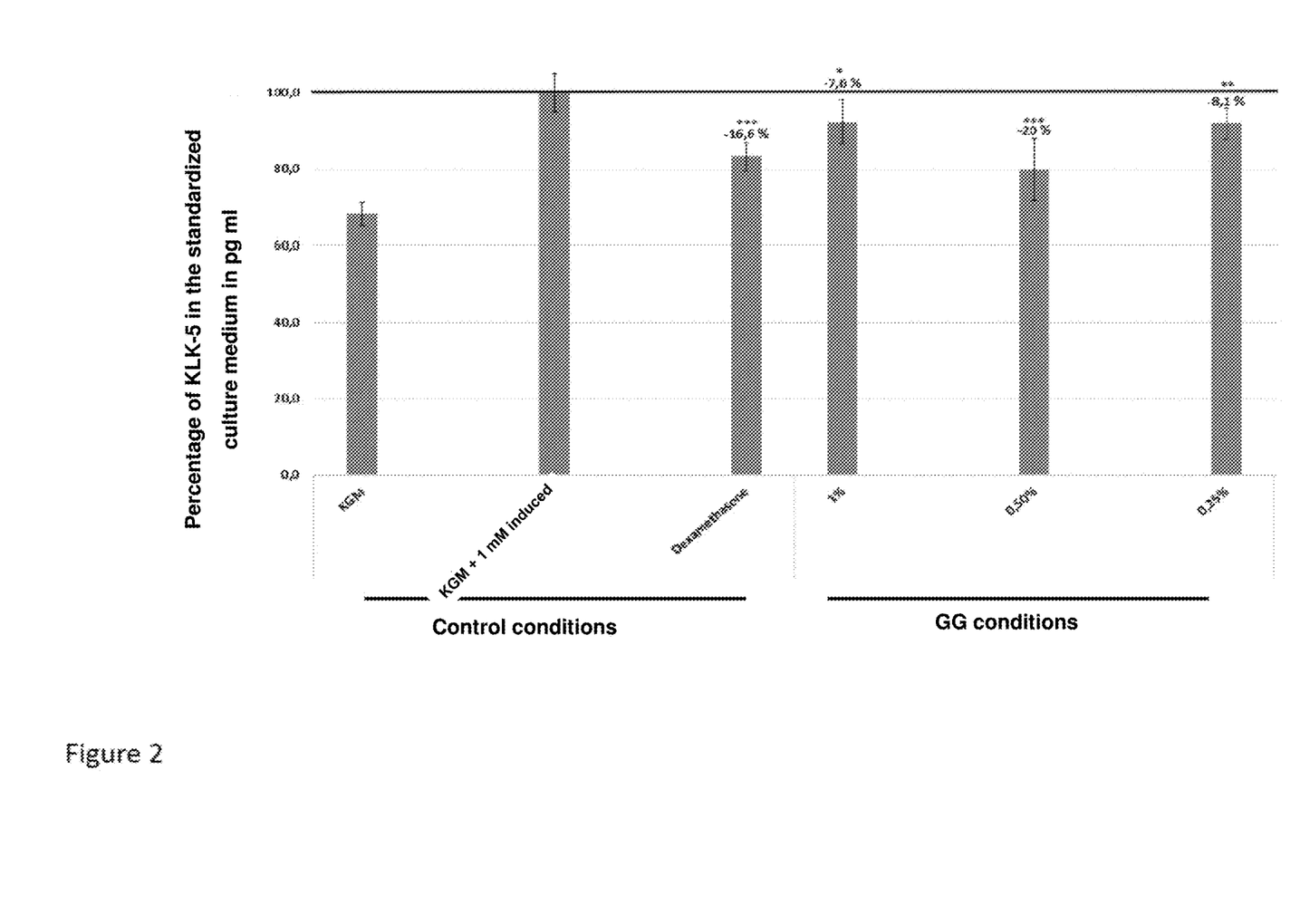
FIG. 2 shows the effect of the glycogen polysaccharide (INCI; hereinafter referred to as gGG) on the inhibition of the synthesis of KLK-5 secreted by normal human keratinocytes (NHK) after 48 hours of incubation. The positive control selected is dexamethasone at 1 µM. The results are expressed as a percentage of expression normalized to cell viability. They represent the data obtained on 1 experiment carried out in triplicate.

The results are represented in FIGS. 1 and 2 in the form of a graph.

In accordance with what was expected for the control condition, 1 μM dexamethasone inhibits the synthesis of KLK-5 by 16.6%.

The combination of MOG+HSH polysaccharides (maltooligosyl glucoside & hydrogenated starch hydrolysate; INCI) according to the invention significantly reduces the synthesis of KLK-5 by 21.5%, 27.3% and 26.7% respectively at doses by 1%, 0.5% and 0.25% (FIG. 1).

The GG polysaccharide (glycogen; INCI) according to the invention decreases the synthesis of KLK-5 significantly by 7.6%, 20% and 8.1% respectively at doses of 1%, 0.5% and 0.25%.

This study clearly demonstrates that the combination of maltooligosyl glucoside & hydrogenated starch hydrolysate polysaccharides (INCI; MOG+HSH or glycogen polysaccharide (INCI; GG) according to the invention significantly reduce the synthesis of KLK-5 by normal human keratinocytes grown in an environment mimicking rosacea.

The invention claimed is:

1. A method of treatment of rosacea and/or telangiectasia comprising administering to a human subject a composition comprising, as dermatological active ingredient, a glucose and trehalose heteropolymer, wherein the glucose and trehalose heteropolymer comprises a mixture of oligosaccharides in which one, two, three, of or four glucose residues are linked to a trehalose residue.

2. The method according to claim 1, wherein the glucose and trehalose heteropolymer is a mixture comprising maltotriosyl glucoside in an amount of between 40% and 90% by weight of the total mixture.

3. The method according to claim 2, wherein the glucose and trehalose heteropolymer is a mixture comprising maltotriosyl glucoside in an amount of between 50% and 80% by weight of the total mixture.

4. The method according to claim 1, wherein the glucose and trehalose heteropolymer corresponds to the INCI designation maltooligosyl glucoside.

5. The method according to claim 1, wherein the glucose and trehalose heteropolymer represents between 0.001% and 2% by weight of the composition.

6. The method according to claim 5, wherein the glucose and trehalose heteropolymer is maltooligosyl glucoside.

7. The method according to claim 5, wherein the glucose and trehalose heteropolymer represents between 0.01% and 0.5% by weight of the composition.

8. The method according to claim 1, further comprising a branched hydrogenated glucose homopolymer comprising α (1-4) and α (1-6) bonds.

9. The method according to claim 8, wherein the branched hydrogenated glucose homopolymer comprising α (1-4) and α (1-6) bonds, represents between 0.001% and 2% by weight of the composition.

10. The method according to claim 9, wherein the branched hydrogenated glucose homopolymer comprising α (1-4) and α (1-6) bonds is hydrogenated starch hydrolysate.

11. The method according to claim 9, wherein the branched hydrogenated glucose homopolymer comprising α (1-4) and α (1-6) bonds represents between 0.01% and 0.5% by weight of the composition.

12. The method according to claim 8, wherein the branched hydrogenated glucose homopolymer comprising α-(1-4) and α-(1-6) bonds is hydrogenated starch hydrolysate.

13. The method according to claim 1, wherein the composition is a cosmetic composition.

* * * * *